United States Patent
Yoda et al.

(10) Patent No.: US 8,236,911 B2
(45) Date of Patent: Aug. 7, 2012

(54) WATER-SOLUBLE RESIN, HAIR COSMETIC MATERIAL CONTAINING THE SAME, AND SILICONE OIL ADSORPTION ASSISTANT

(75) Inventors: Shoya Yoda, Yokkaichi (JP); Tomoaki Hiwatashi, Yokkaichi (JP); Yuko Yoda, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 12/890,359

(22) Filed: Sep. 24, 2010

(65) Prior Publication Data

US 2011/0014147 A1    Jan. 20, 2011

Related U.S. Application Data

(63) Continuation of application No. 10/588,514, filed as application No. PCT/JP2005/002367 on Feb. 9, 2005, now abandoned.

(30) Foreign Application Priority Data

Feb. 9, 2004 (JP) ................................. 2004-032203
Jan. 25, 2005 (JP) ................................. 2005-016988

(51) Int. Cl.
*C08F 220/28* (2006.01)
*C08F 220/36* (2006.01)

(52) U.S. Cl. ................... 526/303.1; 424/70.17; 526/304

(58) Field of Classification Search ............... 526/303.1, 526/304; 424/70.17
See application file for complete search history.

(56) References Cited

U.S. PATENT DOCUMENTS

| | | | |
|---|---|---|---|
| 5,221,530 A | 6/1993 | Janchitraponvej et al. | |
| 6,123,933 A | 9/2000 | Hayama et al. | |
| 6,375,932 B1 | 4/2002 | Hiwatashi et al. | |
| 6,569,968 B1 | 5/2003 | Hamabe et al. | |
| 2004/0223933 A1 | 11/2004 | Hiwatashi et al. | |
| 2005/0063918 A1 | 3/2005 | Charmot et al. | |
| 2005/0249692 A1 | 11/2005 | Hiwatashi et al. | |

FOREIGN PATENT DOCUMENTS

| | | | |
|---|---|---|---|
| DE | 19532229 | * | 3/1997 |
| JP | 0 080 976 A1 | | 6/1983 |
| JP | 58-103546 | | 6/1983 |
| JP | 03227489 | | 10/1991 |
| JP | 7 69845 | | 3/1995 |
| JP | 11-130822 | | 5/1999 |
| JP | 11130822 A | * | 5/1999 |
| JP | 2000 302649 | | 10/2000 |
| JP | 2003 34704 | | 2/2003 |
| JP | 2003-81742 | | 3/2003 |
| JP | 2003 146852 | | 5/2003 |
| JP | 2003 212733 | | 7/2003 |
| JP | 2003-277243 | | 10/2003 |
| JP | 2003 277794 | | 10/2003 |
| JP | 2005 75861 | | 3/2005 |

OTHER PUBLICATIONS

Office Action issued Mar. 11, 2011, in Korean Patent Application No. 10-2006-7015669 with English translation.
Office Action issued Apr. 5, 2011, 2011, in Japanese Patent Application No. 2005-016988 with English translation.
Office Action issued Nov. 22, 2011, in Korean Patent Application No. 2006-7015669 with English translation.

* cited by examiner

*Primary Examiner* — David W Wu
*Assistant Examiner* — Chun-Cheng Wang
(74) *Attorney, Agent, or Firm* — Oblon, Spivak, McClelland, Maier & Neustadt, L.L.P.

(57) ABSTRACT

Provided is a water-soluble resin which gives a conditioning effect when it is used in a hair cosmetic material containing an anionic surfactant, or the like. A water-soluble resin having a structure corresponding to a copolymer of a monomer mixture containing a vinylic monomer (A) having a hydroxyl group and an amido bond, and a vinylic monomer (B) having a cationic group.

21 Claims, No Drawings

WATER-SOLUBLE RESIN, HAIR COSMETIC MATERIAL CONTAINING THE SAME, AND SILICONE OIL ADSORPTION ASSISTANT

CROSS-REFERENCE TO RELATED APPLICATIONS

The present application is a continuation of a U.S. application Ser. No. 10/588,514, filed Nov. 17, 2006, now abandoned, which is a national stage of a PCT application PCT/JP05/002367, filed Feb. 9, 2005. The present application claims the benefits of priority to the U.S. application Ser. No. 10/588,514, and the contents of that application are hereby incorporated by reference in their entirety. The present application claims the benefits of priority also to Japanese Patent Application No. 2004-032203, filed Feb. 9, 2004, and Japanese Patent Application No. 2005-016988, filed Jan. 25, 2005.

TECHNICAL FIELD

The present invention relates to a water-soluble resin, and in particular, it relates to a water-soluble resin, when used as a hair cosmetic material containing an anionic surfactant, which gives conditioning effects such as good touch in finger-combing in rinsing, a smooth feel after dried and a silky feel after dried, to hairs treated with the hair cosmetic material.

BACKGROUND ART

A conditioner is blended with a hair cosmetic material such as shampoo, hair rinse, hair treatment, and hair styling products in order to improve a touch in finger-combing in rinsing, a touch in combing after washed, a soft feel after washed, and other feels. For example, it is known to blend a cationated hydroxycellulose, a cationated guar gum, a dimethyldiallylammonium chloride/acrylamide copolymer, or the like as a conditioner with a shampoo.

A shampoo having a cationated hydroxylcellulose or the like blended therewith has a good touch in finger-combing in rinsing, but hairs after dried may have a rough feel and a stiff feel. Therefore, to improve this, addition of an oil, co-use of a surfactant, and the like are investigated. Above all, it is known that feels after dried greatly varies by adding a silicone oil (for example, JP-A-2003-212733).

Further, because it is essential that a conditioner is adsorbed on hairs, an amino acid-modified cationated polymer is proposed as a conditioner having improved a sticky feel and a slimy feel, while having proper absorbability, and sustaining the conditioning effect without washing out in rinsing (for example, JP-A-2003-34704).

DISCLOSURE OF THE INVENTION

However, according to the investigations by the present inventors, further high conditioning effect may be required. Further, if a silicone oil is added to the hair cosmetic material, a large amount of a cationated hydroxyethyl cellulose or the like is required in order to adhere a sufficient amount of the silicone oil on hairs. As a result, the hair cosmetic material also gives a rough feel. Further, in the case of hairs damaged by bleaching, coloring or the like (hereinafter sometimes referred to as "damaged hairs"), an adsorption amount of the silicone oil may be small, and thus a sufficient conditioning effect was not obtained.

The present invention is to solve the above problems, and it is, for example, an object to provide a water-soluble resin which gives a conditioning effect when it is used in a hair cosmetic material containing an anionic surfactant, or the like.

As a result of keen investigations in view of the above problems, the present inventors have found that hair cosmetic material containing a water-soluble resin having a structure corresponding to a copolymer of a vinylic monomer having a hydroxyl group and an amido bond, and a vinylic monomer having a cationic group show good conditioning effects, and further increases an adsorption amount of a silicone oil when the silicone oil is used together, and have completed the invention.

That is, a gist of the invention resides in a water-soluble resin having a structure corresponding to a polymerized product of a monomer mixture containing a vinylic monomer (A) having a hydroxyl group and an amido bond, and a vinylic monomer (B) having a cationic group.

Another gist of the invention is a hair cosmetic material containing the water-soluble resin, an anionic surfactant and water.

Specifically, the invention has been achieved by the following means.

(1) A water-soluble resin having a structure corresponding to a copolymer of a monomer mixture containing a vinylic monomer (A) having a hydroxyl group and an amido bond, and a vinylic monomer (B) having a cationic group.

(2) The water-soluble resin of (1), wherein the vinylic monomer (A) having a hydroxyl group and an amido bond is represented by the formula (1):

$$CH_2=C(R^1)-CO-NR^2-(CH_2)_a-OH \qquad (1)$$

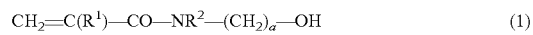

wherein $R^1$ represents a hydrogen atom, or a methyl group; $R^2$ represents a hydrogen atom, or an alkyl group or a hydroxyalkyl group having 1 to 4 carbon atoms; a is an integer from 1 to 4.

(3) The water-soluble resin of (2), wherein a in the formula (1) is 2.

(4) The water-soluble resin of any one of (1) to (3), wherein the vinylic monomer (A) having a hydroxyl group and an amido bond is hydroxyethyl acrylamide, or hydroxyethyl methacrylamide.

(5) The water-soluble resin of any one of (1) to (4), wherein the vinylic monomer (B) having a cationic group is represented by the formula (2):

$$CH_2=C(R^3)-CO(O)_b-(NH)_{1-b}-(CH_2)_c-N^+R^4R^5R^6.X^- \qquad (2)$$

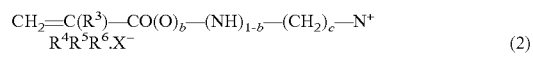

wherein $R^3$ represents a hydrogen atom, or a methyl group; $R^4$ and $R^5$ each independently represent an alkyl group or an aryl group or an aralkyl group having 1 to 24 carbon atoms; $R^6$ represents a hydrogen atom, an alkyl group or an aryl group or an aralkyl group having 1 to 24 carbon atoms, or $CH_2-CH(OH)-CH_2-N^+R^7R^8R^9.Y^-$; $R^7$ to $R^9$ each independently represent an alkyl group or an aryl group or an aralkyl group having 1 to 24 carbon atoms; $X^-$ and $Y^-$ each independently represent an anion; b represents 0, or 1; and c represents an integer from 1 to 10.

(6) The water-soluble resin of any one of (1) to (5), wherein the vinylic monomer (B) having a cationic group is at least one selected from the group consisting of meth acryloxyethyl-trimethylammonium chloride, acroylaminopropyl-trimethylammonium chloride, and meth acroylaminopropyl-trimethylammonium chloride.

(7) The water-soluble resin of any one of (1) to (6), wherein the monomer mixture containing a vinylic monomer (A) having a hydroxyl group and an amido bond, and a vinylic monomer (B) having a cationic group contains 20 to 90% by weight of the vinylic monomer (A) having a hydroxyl group and an amido bond, and 10 to 80% by weight of the vinylic monomer (B) having a cationic group.

(8) The water-soluble resin of any one of (1) to (7), wherein weight average molecular weight is 5,000 to 5,000,000.

(9) The water-soluble resin of any one of (1) to (8), wherein the water soluble-resin can form an aqueous solution having a concentration of at least 5% by weight.

(10) The water-soluble resin of any one of (1) to (9), wherein the vinylic monomer (A) having a hydroxyl group and an amido bond is hydroxyethyl acrylamide, and the vinylic monomer (B) having a cationic group is at least one selected from the group consisting of (meth)acroyloxyethyl-trimethylammonium chloride, acroylaminopropyltrimethylammonium chloride, and (meth)acroylaminopropyltrimethylammonium chloride.

(11) A hair cosmetic material containing the water-soluble resin of any one of (1) to (10).

(12) The hair cosmetic material of (11), further containing an anionic surfactant.

(13) The hair cosmetic material of (12), which is an aqueous solution containing 0.05 to 5% by weight of the water-soluble resin and 5 to 40% by weight of the anionic surfactant.

(14) A silicone oil adsorption assistant comprising the water-soluble resin of any one of (1) to (10).

DETAILED DESCRIPTION OF THE INVENTION

The invention is described in detail hereinafter. In the present specification, the expression "to" is used in the meaning of including the numerical values described at positions before and after the expression as the lower limit and the upper limit. Unless otherwise specifically indicated, the concentration as referred to herein is at 25° C.

The water-soluble resin relate to the invention has a structure corresponding to a copolymer of a monomer mixture containing a vinylic monomer (A) having a hydroxyl group and an amido bond, and a vinylic monomer (B) having a cationic group. The vinylic monomer (A) having a hydroxyl group and an amido bond is preferably a hydroxyalkyl (meth) acrylamide monomer ("(meth)acryl" as referred means acryl and methacryl).

$$CH_2=C(R^1)-CO-NR^2-(CH_2)_a-OH \quad (1)$$

wherein $R^1$ represents a hydrogen atom or a methyl group; $R^2$ represents a hydrogen atom, or an alkyl group or a hydroxyalkyl group having 1 to 4 carbon atoms; a is an integer from 1 to 4.

$R^1$ is preferably a hydrogen atom. $R^2$ is preferably a hydrogen atom, or a methyl group, with a hydrogen atom being more preferable. a is preferably 2.

The vinylic monomer (A) having a hydroxyl group and an amido bond of the formula (1) includes N-hydroxyalkyl (meth)acrylamides such as N-hydroxyethyl (meth)acrylamide, N-hydroxypropyl (meth)acrylamide, and N,N-dihydroxyethyl (meth)acrylamide. Of those, preferred is N-hydroxyethyl (meth)acrylamide, as its solubility in water is high and the solubility in water of the polymer obtained from it is also high.

Preferably, the content of the structural unit corresponding to the vinylic monomer (A) having a hydroxyl group and an amido bond in the copolymer is from 20 to 90% by weight, more preferably from 30 to 80% by weight, even more preferably from 40 to 70% by weight. It is considered that the structural unit corresponding to the vinylic monomer (A) having a hydroxyl group and an amido bond increases the effect of adsorbing on hairs by the action of a hydrogen bond derived from the amido bond portion. It is believed that, when an anionic surfactant is used in hair cosmetic material, the anionic surfactant and a water-soluble resin in the material may form a complex, and when the hair cosmetic material is applied to hair or while the hair is shampooed or rinsed with it, then the complex may deposits and adhere to the hair. In the water-soluble resin of the invention, however, after a structural unit corresponding to the vinylic monomer (B) having a cationic group in the copolymer has formed the complex with the anionic surfactant used together, the copolymer may still keep its solubility in water owing to the hydrophilicity of the structural unit corresponding to the vinylic monomer (A) having a hydroxyl group and an amido bond.

When the content of the structural unit corresponding to the vinylic monomer (A) having a hydroxyl group and an amido bond is at least 20% by weight, adsorption force to hairs or the like may effectively be kept, and, a smooth feel and a silky feel of dried hair are further improved. When it is at least 90% by weight, the content of the structural unit corresponding the vinylic monomer (B) having a cationic group is further sufficiently kept, further sufficient complex with the anionic surfactant can be formed, adsorption amount to hairs is improved, and it is more effective by, for example, a smooth feel of hair in rinsing.

The vinylic monomer (B) having a cationic group includes diallyl-type quaternary ammonium salts such as N,N-dimethyl-N,N-diallylammoniumchloride; (meth)acrylester-type quaternary ammonium salts such as N-methacryloyloxy-ethyl-N,N,N-trimethylammonium chloride; (meth)acrylamide-type quaternary ammonium salts such as N-mathacry-loylaminopropyl-N,N,N-trimethylammonium chloride; amino acid-type cation species such as reaction product of L-arginine and glycidyl methacrylate; and the like. Of those, more preferred are (meth)acryl quaternary ammonium salt monomers. In particular, more preferred are (meth) acryl quaternary ammonium salt monomers of the formula (2).

$$CH_2=C(R^3)-CO(O)_b-(NH)_{1-b}-(CH_2-)_c-N^+R^4R^5R^6.X^- \quad (2)$$

wherein $R^3$ represents a hydrogen atom, or a methyl group; $R^4$ and $R^5$ each independently represent an alkyl group or an aryl group or an aralkyl group having 1 to 24 carbon atoms; $R^6$ represents a hydrogen atom, an alkyl group or an aryl group or an aralkyl group having 1 to 24 carbon atoms, or $CH_2-CH(OH)-CH_2-N^+R^7R^8R^9.Y^-$; $R^7$ to $R^9$ each independently represent an alkyl group or an aryl group or an aralkyl group having 1 to 24 carbon atoms; $X^-$ and $Y^-$ each independently represent an anion; b represents 0, or 1; and c represents an integer from 1 to 10.

Preferably, $R^3$ is a methyl group. Preferably, $R^4$ and $R^5$ are each independently a methyl group or an ethyl group, and more preferably a methyl group. Preferably, $R^6$ is a methyl group, an ethyl group or a butyl group, and more preferably a methyl group. Preferably, $R^7$ to $R^9$ are each independently a methyl group or an ethyl group, and more preferably a methyl group. Preferably the anions for $X^-$ and $Y^-$ are each independently a chlorine ion, an iodine ion or a bromine ion. Preferably, b is 0. Preferably, c is an integer from 1 to 5, and more preferably 3.

Some vinylic monomers having a cationic group of the formula (2) are exemplified below; cationic group having (meth)acrylic esters, such as N-(meth)acryloyloxyethyl-N,N,N-trimethylammonium chloride, N-(meth) acryloyloxyethyl-N-ethyl-N,N-dimethylammonium=monoethyl sulfate salt, N-(meth)acryloyloxyethyl-N,N,N-triethylammonium=monoethyl sulfate salt, N-[3-{N'-(meth) acryloyloxyethyl-N',N'-dimethylammonium}-2-hydroxypropyl]-N,N,N-trimethylammonium chloride, N-[3-{N'-(meth)acryloyloxyethyl-N',N'-diethylammonium}-2-hydroxypropyl]-N—,N,N-trimethylammonium chloride; and cationic group-having (meth) acrylamides such as N-(meth)acryloylaminopropyl-N,N,N-trimethylammonium chloride, N-(meth)acryloylaminopropyl-N-methyl-N,N-dimethylammonium=monoethyl sulfate salt, N-(meth)acryloylaminopropyl-N,N-diethyl-N-methylammonium chloride, N-(meth)acryloylaminopropyl-N,N-diethyl-N-methylammonium=monomethyl sulfate salt, N-[3-{N'-(meth)acryloylaminopropyl-N',N'-dimethylammonium}-2-hydroxypropy-1]-N,N,N-trimethylammonium chloride, and N-[3-{N'-(meth)acryloylaminopropyl-N',N'-diethylammonium}-2-hydroxypropyl-]-N,N,N-trimethylammonium chloride; and the like.

Of those, preferred are N-(meth)acryloyloxyethyl-N,N,N-trimethylammonium chloride and N-(meth)acryloylaminopropyl-N,N,N-trimethylammonium chloride, and more preferred is N-(meth)acryloylaminopropyl-N,N,N-trimethylammonium chloride.

The structure corresponding to the copolymer of the cationic group-having vinylic monomer (B) may be prepared, for example, by copolymerizing with vinylic monomer precursor having a cationic group of the formula (3), and then by converting into the corresponding structure having a cationic group by a cationating agent.

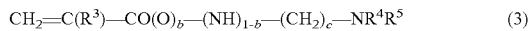

$$CH_2=C(R^3)-CO(O)_b-(NH)_{1-b}-(CH_2)_c-NR^4R^5 \quad (3)$$

wherein, $R^3$ to $R^5$, b and c are the same as defined in the formula (2), and the preferable range is also the same as defined therein.

The cationic vinylic monomer precursor includes, for example, (meth)acrylates esters having a tertiary amine such as N-(meth)acryloyloxyethyl-N,N-dimethylamine, N-(meth)acryloyloxyethyl-N,N-diethylamine; and (meth)acrylamides having a tertiary amine such as N-(meth)acryloylaminopropyl-N,N-dimethylamine, N-(meth)acryloylaminopropyl-N,N-diethylamine; and the like.

The cationating agent includes an alkyl halide such as methyl chloride; a cationating agents having cationic group such as 3-chloro-2-hydroxypropyl-N,N,N-trimethylammonium chloride, and the like. Cationation can be conducted, for example, by adding the cationating agent to a solution of a polymer, and reacting them at the conditions 20 to 100° C. and 1 to 20 hours.

One or more different types of cationic vinylic monomers or their precursors may be used herein singly or as combined.

Preferably, the content of the structural unit corresponding to the vinylic monomer (B) having a cationic group in the copolymer is 10 to 80% by weight, more preferably 20 to 70% by weight, and particularly more preferably 30 to 60% by weight. The structural unit corresponding to the vinylic monomer (B) having a cationic group may form a complex with the anionic surfactant in hair cosmetic material, thereby making the copolymer more adhere to hair. When the content of the structural unit corresponding to the vinylic monomer (B) having a cationic group is at least 10% by weight, then it may form a sufficient complex with the anionic surfactant, for example, the hair cosmetic material may be more effective for keeping the shampooed hair smooth during rinsing. When the content of the structural unit is at most 80% by weight, adsorption force to hairs and the like can further sufficiently be kept better, and as a result, a smooth feel and a silky feel of hair after dried can further effectively be kept.

The copolymer may further contain a structural unit derived from other vinylic monomer. However, if an anionic functional group is present in the copolymer, then it may interfere with the formation of the complex with the above-described anionic surfactant. Therefore, it is desirable that the amount of such an anionic functional group in the copolymer is as small as possible (for example, at most 10% of the total functional groups in the copolymer). More preferably, the copolymer does not substantially contain the group. The term "not substantially contain" means, for example, not showing anionic property at pH 3 to 8. Any other vinylic monomer includes esters of (meth) acrylic acid with an alcohol having from 1 to 22 carbon atoms; amides of (meth) acrylic acid with an alkylamine having from 1 to 22 carbon atoms; monoesters of ethylene glycol or 1,3-propylene glycol or the like with (meth) acrylic acid; esters derived from the monoesters by etherifying the hydroxyl group therein with methanol ethanol or the like; nonionic monomers such as (meth) acryloylmorpholine; amphoteric monomers such as betaine group-having (meth)acryl esters, betaine group-having (meth)acrylamides; semi-polar monomers such as amine oxide group-having (meth)acryl esters, amine oxide group-having (meth)acrylamides; and the like.

The content of the structural unit derived from the other vinylic monomer may appropriately be determined within a range within the scope which does not overlap the subject matter of the invention. For example, the content may appropriately be determined within a range not disturbing solubility of the water-soluble resin, conditioning effect where used in hair cosmetic material, and the like. Preferably, the content of the other vinylic copolymer is at most 30% by weight.

The contents of the structural unit corresponding to the vinylic monomer (A) having a hydroxyl group and an amido bond, the structural unit corresponding to the vinylic monomer (B) having a cationic group, and the structural unit derived from the other vinylic monomer, in the copolymer can be determined by IR absorption of a hydroxyl group or an amido bond site, $^1$H-NMR of a hydroxyl group, an amido bond site, or a methyl group adjacent to the cationic group, $^{13}$C-NMR of those, and the like.

Preferably, the water-soluble resin of the invention is a resin capable of forming an aqueous solution having a concentration of at least 5% by weight at an ordinary temperature, i.e., 25° C., that is, a resin in which an aqueous solution having a concentration of at least 5% by weight has a transmission (550 nm) of at least 80%, and the aqueous solution is uniform and stable. More preferably, the resin may from an aqueous solution having a concentration of at least 20% by weight.

The water-soluble resin according to the present invention may be prepared, for example, by mixing monomers or their precursors giving the respective structural units, copolymerizing by a method such as solution polymerization, suspension polymerization or emulsion polymerization, and then, optionally, cationating the resulting copolymer.

Preferably the polymerization is conducted in a hydrophilic solvent. The hydrophilic solvent includes ketone solvents such as acetone, methyl ethyl ketone and methyl isobutyl ketone; alcohol solvents such as methanol, ethanol, n-propanol, i-propanol, n-butanol, butanol and sec-butanol; and water. One or more of these may be used herein either singly or as combined. Preferred are alcohol solvents or water.

The polymerization initiator usable herein is not specifically defined, including, azo compounds such as 2,2'-azobisisobutyronitrile, 2,2'-azobis(2,4-dimethylvaleronitrile), 2,2'-azobis(4-methoxy-2,4-dimethylvaleronitrile), dimethyl-2,2'-azobisisobutyronitrile, 2,2'-azobis(2-methylbutyronitrile), 1,1'-azobis(1-cyclohexanecarbonitrile), 2,2'-azobis(2-methyl-N-(2-hydroxyethyl)-propionamide), 2,2'-azobis(2-amidinopropane) dihydrochloride; peroxides such as benzoyl peroxide, dicumyl peroxide, di-t-butyl peroxide, lauroyl peroxide; persulfates; and their redox type agent; and the like. Preferably the amount of the polymerization initiator to be used is from 0.01 to 5% by weight of all the monomers.

The polymerization may be conducted in an inert gas atmosphere such as nitrogen or argon, at preferably 30 to 120° C., and more preferably 40 to 100° C., for 1 to 30 hours. After completion of the polymerization, the copolymer formed may be isolated from the reaction solution in an appropriate method such as solvent distilling off or addition of poor solvent. The copolymer may be used to the production of hair cosmetic material and the like according to the invention directly or after further purification. The purification maybe conducted by an appropriate method such as reprecipitation, solvent washing or membrane separation, or by combing the methods thereof.

Weight average molecular weight of the copolymer of the invention is preferably 5,000 to 5,000,000, more preferably 10,000 to 2,000,000, and further preferably 20,000 to 1,000,000. When the weight average molecular is at least 5,000, adsorption force to hairs can be increased, and conditioning effect can further effectively be kept. When the weight average molecular weigh is at most 5,000,000, viscosity can appropriately be kept, resulting in easy handling on production. The weight average molecular weight of the copolymer may be determined by gel permeation chromatography (for example, using water/methanol/acetic acid/sodium acetate as a developing solvent).

The water-soluble resin of the invention increases adsorption amount of a silicone oil on hairs, and can be used as a silicone oil adsorption assistant. It is preferable that the silicone oil adsorption amount on hairs is preferably 70 ppm or more, with being more preferably 100 ppm or more.

Further, the silicone oil adsorption amount on hairs is preferably 5,000 ppm or less, and more preferably 2,000 ppm or less. By making the amount be 5,000 ppm or less, hairs after dried can be prevented from being sticky, which is preferable.

Further, preferably, the silicone oil adsorption amount on bleach-treated hairs is within the above range.

The hair cosmetic material of the invention may be prepared by blending a necessary amount of the water-soluble resin obtained by the above method with a formulation. Other components to be contained in the hair cosmetic material are not particularly limited, and may be blended within a range which does not disturb the object and effect of the invention. Concretely, such other components are an anionic surfactant, a cationic surfactant, a nonionic surfactant, a water-soluble polymer other than the water-soluble resin of the invention, cationic polymer, an anionic polymer, a nonionic polymer, an amphoteric polymer, an oil component, a pearly agent, and the like.

When the water-soluble resin obtained by the above method is, for example, used in a shampoo or the like, it can be prepared by dissolving the water-soluble resin into water. In this case, the concentration of the anionic surfactant is preferably 5 to 40% by weight, and more preferably 10 to 30% by weight, and the concentration of the water-soluble resin is preferably 0.05 to 5% by weight, and more preferably 0.1 to 1% by weight. When the anionic surfactant and the water-soluble resin is within the above concentration ranges, the anionic surfactant and the water-soluble resin forms a complex in the hair cosmetic material obtained, and this complex deposits to adhere on hairs in shampooing or rinsing, thereby giving a good touch of hair in finger-combing.

When the concentration of the anionic surfactant is at less 5% by weight, the hair cosmetic material can further effectively exhibit the function, and reversely when it is at most 40% by weight, viscosity can appropriately be kept, making it easy to handle. When the concentration of the water-soluble resin is at least 0.05% by weight, the conditioning effect can further effectively be exhibited, thereby improving a touch of hair in finger-combing and the like.

The anionic surfactant includes materials that are generally used in hair cosmetic material, such as α-olefin sulfonic acid salt, a higher alcohol sulfuric ester salt, a polyoxyethyl alkyl ether sulfuric ester salt, a paraffin sulfonate, a polyoxyethylene alkyl ether carboxylic ester salt, an alkylsulfosuccinate, N-acyl-β-alanine salt, N-acylglutamate, and acylmethyltaurinate. The counter ion of those anionic surfactants includes sodium, potassium, ammonium, triethanolamine, diethanolamine, and the like. The anionic surfactants may be used in combination of several kinds.

Other optional components that can be blended with hair cosmetic material are exemplified below.

The cationic surfactant includes stearyl trimethylammonium chloride, behenyl trimethylammonium chloride and the like. The cationic surfactant can effectively improve feels. Preferably, an amount of the cationic surfactant is 0.1 to 3% by weight.

The nonionic surfactant includes alkanol amide, glycerin fatty acid ester, polyoxyethyelene-hardened caster oil, polyoxyethylene alkyl ether and the like. The amphoteric surfactant includes alkylamide propyl betaine, alkylcarboxybetaine, alkylsulfobetaine and the like. Preferably an amount of those is 1 to 10% by weight.

The water-soluble polymer other than the water-soluble resin of the invention includes methyl cellulose, hydroxymethyl cellulose and the like. The cationic polymer includes a cation-modified cellulose ester derivative, a polydimethyldiallylammonium halide, a copolymer of dimethyldiallylammonium halide and acrylamide, and the like. The anionic polymer includes an acrylic acid derivative (a polyacrylic acid and its salt, an acrylic acid-acrylamide-ethyl acrylate copolymer and its salt, etc.), a methacrylic acid derivative, a crotonic acid derivative, and the like. The nonionic polymer includes an acrylic acid derivative (a hydroxyethyl acrylate-methoxyethyl acrylate copolymer, a polyacrylamide, etc.), and a vinylpyrrolidone derivative (a polyvinylpyrrolidone, a vinylpyrrolidone-vinyl acetate copolymer, etc.). The amphoteric polymer includes a dimethyldiallylammonium chloride derivative (an acrylamide-acrylic acid-dimethyldiallylammonium chloride copolymer, an acrylic acid-dimethyldiallylammonium chloride copolymer, etc.), and the like. Preferably, an amount of those is 0.1 to 1% by weight.

The oil component includes a higher alcohol, a silicone oil, an olive oil, a jojoba oil, a liquid paraffin, a fatty acid alkyl ester oil, and the like. Of those, when a silicone oil is blended, a silky feel after dried is further improved. Therefore, the silicone oil is particularly useful. The silicone oil desirably is used involatile polydimethylsiloxanes. Preferably, an amount of the oil component is 0.1 to 2% by weight.

A pearly agent includes ethylene glycol fatty acid, and the like, and a suspending agent includes a polystyrene-emulsified product and the like. Preferably, an amount of those is 0.1 to 2% by weight.

As other component, natural extracts of animals and plants, and their derivatives, an inorganic salt such as sodium chloride, a solubilizing agent (ethanol, ethylene glycol, propylene glycol, etc.), a moisturizer (glycerin, sorbitol, maltitol, dipropylene glycol, 1,3-butyrene glycol, hyaluronic acid, etc.), an antioxidant, a higher fatty acid, a thickening agent, a sequestering agent (edentate, etc.), a pH regulator, an ultraviolet absorber, a sterilizer, a preservative, a dyestuff, a perfume, a lathering booster, and the like may appropriately be blended in a range that does not disturb the effect of the invention.

EXAMPLE

The present invention is further specifically described below using the examples, but the invention is not limited by the following examples so long as it is not beyond the gist of the invention.

Example 1

Production of Copolymer (1)

300 parts by weight of distilled water were placed in a reactor equipped with a reflux condenser, a dropping funnel, a thermometer, a nitrogen gas introduction pipe, and a stirring means, and a monomer mixed liquid of monomers (copolymer (1)) in Table 1 and 100 parts by weight of distilled water was placed in the dropping funnel. The reactor was replaced with nitrogen, and heated up to 70° C. 0.5 part by weight of 2,2'-azobis (2-amidinopropane)-dihydrochloride was introduced into the reactor, and the monomer mixture was then added dropwise over 1 hour. After conducted the reaction for 4 hours from the addition of dropwise, the reactor was heated to 80° C., and reaction was further conducted for 2 hours.

Weight average molecular weight of the copolymer obtained was determined using a gel permeation chromatography (apparatus, Tosoh's SC8010, SD8022, RI8020, C08011, PS8010; column, Wako Jun-yaku's Wakopack (Wakobeads G-50); developer solvent: water/methanol/acetic acid/sodium acetate=6/4/0.3/0.41). The results are shown in Table 1.

Water solubility of the copolymer obtained was conducted according to the following criteria by preparing a 5 wt % aqueous solution and a 20 wt % aqueous solution at 25° C. and measuring its transmission (550 nm, 10 mm glass cell). The results are shown in Table 1.

○: 80% or more
Δ: 50% or more to less than 80%
x: Less than 50%

TABLE 1

| | Monomer composition (parts by weight) | | | | | | | | | Average | 5% | 20% |
|---|---|---|---|---|---|---|---|---|---|---|---|---|
| | | Monomer (B) | | | | Monomer (A) | | | | | | |
| | | DMAP | DMAP | DAD | GMA | | | DMAP | | molecular | Water | Water- |
| Copolymer | DMC | AAC | MAC | MAC | Arg | HEAA | NMAA | MAO | HEA | weight | solubility | solubility |
| (1) | 20 | — | — | — | — | 80 | — | — | — | 450000 | ○ | ○ |
| (2) | 40 | — | — | — | — | 60 | — | — | — | 420000 | ○ | ○ |
| (3) | 60 | — | — | — | — | 40 | — | — | — | 360000 | ○ | ○ |
| (4) | — | 40 | — | — | — | 60 | — | — | — | 400000 | ○ | ○ |
| (5) | — | — | 40 | — | — | 60 | — | — | — | 300000 | ○ | ○ |
| (6) | 5 | — | — | — | — | 95 | — | — | — | 320000 | ○ | ○ |
| (7) | 90 | — | — | — | — | 10 | — | — | — | 500000 | ○ | ○ |
| (8) | — | — | — | 40 | — | 60 | — | — | — | 120000 | ○ | ○ |
| (9) | — | — | — | — | 40 | 60 | — | — | — | 280000 | ○ | ○ |
| (10) | — | 40 | — | — | — | — | 60 | — | — | 300000 | ○ | ○ |
| (11) | — | — | 40 | — | — | — | — | 60 | — | 320000 | ○ | ○ |
| (12) | — | 40 | — | — | — | — | — | — | 60 | 100000 | ○ | ○ |

DMC: N-Methacryloyloxyethyl-N,N,N-trimethylammonium chloride
DMAPAAC: N-Acryloylaminopropyl-N,N,N-trimethylammonium chloride
DMAPMAC: N-Methacryloylaminopropyl-N,N,N-trimethylammonium chloride
DADMAC: N,N-Dimethyl-N,N-diallylammonium chloride
GMAArg: Reaction product of L-arginine and glycidyl methacrylate
HEAA: N-Hydroxyethyl acrylamide
NMAA: N-Methylol acrylamide
DMAPMAO: N-Methacryloylaminopropyl-N,N-dimethylamine oxide
HEA: Hydroxyethyl acrylate (Preparation of Hair Cosmetic Material)

A shampoo having this composition was prepared by using the copolymer (1) as a resin shown in Table 2. The preparation was conducted by mixing components other than a silicone oil, and then blending the silicone oil with the resulting mixture. Using the shampoo prepared, lathering, a smooth feel in rinsing, a silky feel of hair after dried, a smooth feel of hair after dried and silicone oil adsorption amount were evaluated by the methods described below.

TABLE 2

| Formulation | wt % as solid content |
|---|---|
| Resin | 0.3 |
| Anionic surfactant *1 | 10 |
| Lauroylamidopropyl betaine | 5 |
| Silicone oil *2 | 2 |

TABLE 2-continued

| Formulation | wt % as solid content |
|---|---|
| MARCOAT 550 *3 | 0.5 |
| Stearyltrimethylammonium chloride *4 | 1 |
| Distilled water | Remnant (Total 100) |

*1: Polyoxyethylene (3) lauryl ether sodium sulfate, LES-Na (a product of Lion Corporation)
*2: Silicone oil emulsion BY22029 (a product of Dow Corning Toray Co., concentration: 50%)
*3: Copolymer of dimethyldiallylammonium halide and acrylamide (a product of Merck & Co., Inc.)
*4: Stearyltrimetylammonium chloride, ARCARD T-28 (a product of Lion Chemical Corporation)

(Evaluation of Hair Cosmetic Material)

The hair cosmetic material obtained by the above method was evaluated by the following method. The evaluation results when non-processed hair bundles were used as a hair bundle are shown in Table 3, and the evaluation results when damaged hairs were used as a hair bundle are shown in Table 4.

Examples 2 to 9

Production of Copolymers (2) to (9)

Copolymers (2) to (9) were produced in the same manner as the production of the copolymer (1), except for using monomer compositions shown in Table 1 (copolymer (2) to (9)). Weight average molecular weight of the copolymers obtained is shown in Table 1.

(Preparation and Evaluation of Hair Cosmetic Material)

Preparation and evaluation of the hair cosmetic material were conducted in the same manners as described in Example 1. The evaluation results are shown in Tables 3 and 4.

Example 10

Production of Copolymer (10)

Copolymer (10) was produced in the same manner as the production of the copolymer (1), except for using the monomer composition described in Table 1 (copolymer (10)) and changing the amount of distilled water introduced into the reactor at the initial stage to 500 parts by weight. Weight average molecular weight of the copolymer obtained is shown in Table 1.

(Preparation and Evaluation of Hair Cosmetic Material)

Preparation and evaluation of the hair cosmetic material were conducted in the same manners as described in Example 1. The evaluation results are shown in Tables 3 and 4.

Comparative Example 1

Production of Copolymer (11)

Copolymer (11) was produced in the same manner as the production of the copolymer (1), except for using the monomer composition described in Table 1 (copolymer (11)). Weight average molecular weight of the copolymer obtained is shown in Table 1.

(Preparation and Evaluation of Hair Cosmetic Material)

Preparation and evaluation of the hair cosmetic material were conducted in the same manners as described in Example 1. The evaluation results are shown in Tables 3 and 4.

Comparative Example 2

Production of Copolymer (12)

Copolymer (12) was produced in the same manner as the production of the copolymer (1), except for using the monomer composition described in Table 1 (copolymer (12)), using ethanol as a solvent, and using dimethyl-2,2'-azobisisobutyrate as a polymerization initiator. Distilled water was added to the copolymer obtained, and ethanol was distilled off to obtain an aqueous solution. Weight average molecular weight of the copolymer obtained is shown in Table 1.

(Preparation and Evaluation of Hair Cosmetic Material)

Preparation and evaluation of the hair cosmetic material were conducted in the same manners as described in Example 1. The evaluation results are shown in Tables 3 and 4.

Comparative Example 3

Preparation and Evaluation of Hair Cosmetic Material

Preparation and evaluation of hair cosmetic material were conducted in the same manners as described in Example 1, except for using a cationated hydroxyethyl cellulose as resin described in Table 2 (Calgon's JR400). The evaluation results are shown in Tables 3 and 4.

Comparative Example 4

Standard (Preparation and Evaluation of Hair Cosmetic Material)

Preparation and evaluation of hair cosmetic material were conducted in the same manners as described in Example 1, except that the resin described in Table 2 was not blended. The evaluation results are shown in Tables 3 and 4.

(Evaluation Method)

Each shampoo composition was applied to a hair bundle provided, and the following items were evaluated respectively. As the hair bundle, "root-trimmed human black hair (100%) (non-processed hair bundles: 10 g×30 cm), by Viewlax)" was used as "non-processed hair bundles". Further, hairs obtained by subjecting "non-processed hair bundles" to the following bleach treatment were used as "damaged hairs". The bleach treatment was conducted by applying a mixture of 12 g of Milbon's Promatis Brave Oxitan 6.0 (hydrogen peroxide 6% cream), and 6 g of Melos Chemical's Powder Bleach MR2, as a bleaching agent to one hair bundle, allowing the same to stand for 30 minutes, washing with water, applying polyoxyethylene (3) lauroyl ether sodium sulfate, and washing.

(1) Lathering

Water was contained in 10 g of a hair bundle with flowing water of 40° C., excess water was removed, and 1 g of a shampoo was applied, and foamed. Degrees of speed of lathering and fineness of foams formed in such a case were evaluated by four levels and ranked.

+2: The sample is better than the standard (with no resin) in point of both the lathering speed and the texture of the later.

+1: The sample is better than the standard in point of either the lathering speed or the texture of the later.

0: The sample is on the same level as the standard.

−1: The sample is inferior to the standard.

(2) Smooth Feel in Rinsing

After evaluation of lathering, smooth feel in finger-through combing in rinsing the hair bundle with flowing water of 40° C., and sustainability of its smooth feel were evaluated by four levels.

+2: The sample is better than the standard in point of the smooth feel, and its smooth feel lasts for 1 minute or more.

+1: The sample is better than the standard in point of either the smooth feel or the smooth feel durability.

0: The sample is on the same level as the standard.

−1: The sample is inferior to the standard.

(3) Silky Feel after Dried

The hair bundle after evaluation of smooth feel in rinsing was dried in a thermostatic chamber at 23° C. and 60% RH overnight, and silky feel of the hair bundle was evaluated by four levels.

+2: The sample is much better than the standard in point of the silky feel.

+1: The sample is better than the standard in point of the silky feel.

0: The sample is on the same level as the standard.

−1: The sample is inferior to the standard.

(4) Softness after Dried

Using the hair bundle after evaluation of Silky feel, softness after dried was evaluated by four levels.

+2: As compared with the standard, the sample does not almost have a rough feel.

+1: The sample has a rough feel in some degree, though better than the standard.

0: The sample is on the same level as the standard.

−1: The sample is inferior to the standard.

(5) Silicone Oil Adsorption

After wetting 10 g of a hair bundle with flowing water of 40° C., water drip was conducted until not dropping water droplets. 1 g of a shampoo was applied to the hair bundle, and the hair bundle was comb 100 times for 1 minute to foam. The hair bundle thus treated was rinsed with flowing water of 40° C. for 30 seconds, and then dried overnight. After repeating this treatment two times, the silicone oil adsorbed on the hairs was extracted, and an adsorption amount was evaluated by NMR measurement (quantitative determination of H in Si—CH$_3$ by $^1$H-NMR) of the extract.

The extraction was conducted by dipping a hair bundle in a solvent of chloroform/methanol=4/1, treating with ultrasonic wave, drying the solvent in reduced pressure, dissolving in heavy chloroform, adding dimethyl terephthalate as an internal standard, and determining a concentration.

after dried, softness after dried, and silicone oil adsorption amount in non-processed hair bundles and damaged hairs are poor.

4) Because Comparative Example 3 uses cationated hydroxyethyl cellulose which does not have an amido bond as the water-soluble resin, softness after dried is poor in non-processed hair bundles and damaged hairs.

TABLE 3

Evaluation result with untreated hair

| | Resin (In Table 2) | Lathering | Smooth feel in rinsing | Silky feel after dried | Softness after dried | Silicone oil adsorption amount (ppm) |
|---|---|---|---|---|---|---|
| Example 1 | Copolymer (1) | +2 | +1 | +2 | +2 | 500 |
| Example 2 | Copolymer (2) | +2 | +1 | +2 | +2 | 700 |
| Example 3 | Copolymer (3) | +2 | +1 | +2 | +1 | 680 |
| Example 4 | Copolymer (4) | +2 | +2 | +2 | +2 | 800 |
| Example 5 | Copolymer (5) | +2 | +2 | +2 | +2 | 750 |
| Example 6 | Copolymer (6) | +1 | +1 | +1 | +2 | 400 |
| Example 7 | Copolymer (7) | +2 | +1 | +2 | +1 | 420 |
| Example 8 | Copolymer (8) | +2 | +1 | +1 | +1 | 350 |
| Example 9 | Copolymer (9) | +2 | +1 | +1 | +1 | 350 |
| Example 10 | Copolymer (10) | +2 | +2 | +1 | +1 | 400 |
| Comparative Example 1 | Copolymer (11) | +2 | +2 | +2 | +2 | 700 |
| Comparative Example 2 | Copolymer (12) | 0 | −1 | −1 | −1 | 280 |
| Comparative Example 3 | JR400 | +2 | +2 | +1 | −1 | 750 |
| Comparative Example 4 (Standard) | (None) | 0 | 0 | 0 | 0 | 300 |

JR400: Cationated hydroxyethyl cellulose

"None" in the Table means that a resin is not blended.

TABLE 4

Evaluation result with damaged hair

| | Resin (In Table 2) | Lathering | Smooth feel in rinsing | Silky feel after dried | Softness after dried | Silicone oil adsorption amount (ppm) |
|---|---|---|---|---|---|---|
| Example 1 | Copolymer (1) | +2 | +1 | +2 | +2 | 200 |
| Example 2 | Copolymer (2) | +2 | +1 | +2 | +2 | 300 |
| Example 3 | Copolymer (3) | +2 | +1 | +2 | +1 | 250 |
| Example 4 | Copolymer (4) | +2 | +2 | +2 | +2 | 400 |
| Example 5 | Copolymer (5) | +2 | +2 | +2 | +2 | 300 |
| Example 6 | Copolymer (6) | +1 | +1 | +1 | +1 | 120 |
| Example 7 | Copolymer (7) | +2 | +1 | +1 | +1 | 150 |
| Example 8 | Copolymer (8) | +2 | 0 | +1 | +1 | 80 |
| Example 9 | Copolymer (9) | +2 | +1 | +1 | 0 | 90 |
| Example 10 | Copolymer (10) | +2 | 0 | +1 | 0 | 70 |
| Comparative Example 1 | Copolymer (11) | +2 | +1 | 0 | +1 | 50 |
| Comparative Example 2 | Copolymer (12) | 0 | −1 | −1 | −1 | 45 |
| Comparative Example 3 | JR400 | +2 | +1 | 0 | −1 | 60 |
| Comparative Example 4 | (None) | 0 | 0 | 0 | 0 | 50 |

(Evaluation of Results)

1) Comprehensively evaluating, Examples 1 to 5 obtained most preferable results, Examples 6 and 7 obtained second preferable results, and Examples 8 to 10 obtained third preferable results.

2) Because Comparative Example 1 uses N-methacryloylaminopropyl-N,N-dimethylamine oxide in the production of a water-soluble resin, the structural unit of the water-soluble resin does not have a hydroxyl group. For this reason, the silicone oil adsorption amount on the damaged hairs is low, and silky feel of hair after dried is poor.

3) Because Comparative Example 2 uses hydroxyethyl acrylate in the production of a water-soluble resin, the structural unit of the water-soluble resin does not have an amido bond. For this reason, lathering, smooth feel in rinsing, silky feel 5) Because Comparative Example 4 (standard sample) does not contain a resin, lathering, smooth feel in rinsing, silky feel after dried, softness after dried, and silicone oil adsorption amount in non-processed hair bundles and damaged hairs are poor as compared with the hair cosmetic material having blended therein the water-soluble resin of the invention.

When the water-soluble resin of the invention is used in, for example, hair cosmetic material comprising an anionic surfactant as a main component, the water-soluble resin gives conditioning effects, such as a good touch of hair in finger-combing in rinsing, smooth feel after dried, silky feel and softness, to hairs treated with the hair cosmetic material, and thus the industrial value of the invention is remarkable.

ADVANTAGE OF THE INVENTION

The water-soluble resin of the invention is excellent in lathering, smooth feel in rinsing, silky feel after dried, softness after dried, and silicone oil adsorption amount. For this reason, conditioning effects and the like when used in hair cosmetic material are excellent.

The invention claimed is:

1. A hair cosmetic material comprising:
a water-soluble resin having a structure corresponding to a copolymer of a monomer mixture comprising a vinylic monomer (A) having a hydroxyl group and an amide bond, and a vinylic monomer (B) having a cationic group,
wherein the vinylic monomer (B) is represented by a formula, $CH_2=C(R^3)-CO(O)_b-(NH)_{1-b}-(CH_2)_c-N^+R^4R^5R^6.X^-$, where $R^3$ represents a hydrogen atom or a methyl group, $R^4$ and $R^5$ each independently represent an alkyl group having 1 to 24 carbon atoms, an aryl group having 6 to 24 carbon atoms, or an aralkyl group having 7 to 24 carbon atoms, $R^6$ represents a hydrogen atom, an alkyl group having 1 to 24 carbon atoms, an aryl group having 6 to 24 carbon atoms, or an aralkyl group having 7 to 24 carbon atoms, or $CH_2-CH(OH)-CH_2-N^+R^7R^8R^9.Y^-$, $R^7$ to $R^9$ each independently represent an alkyl group having 1 to 24 carbon atoms, an aryl group having 6 to 24 carbon atoms, or an aralkyl group having 7 to 24 carbon atoms, $X^-$ and $Y^-$ each independently represent an anion, b represents 0 or 1, and c represents an integer from 1 to 10, wherein the water-soluble resin is in a hair cosmetic composition.

2. The hair cosmetic material of claim 1, wherein the vinylic monomer (A) is hydroxyethyl acrylamide or hydroxyethyl methacrylamide.

3. The hair cosmetic material of claim 1, wherein the vinylic monomer (B) is at least one selected from the group consisting of meth acroyloxyethyl-trimethylammonium chloride, acroylaminopropyl-trimethylammonium chloride, and meth acroylaminopropyl-trimethylammonium chloride.

4. The hair cosmetic material of claim 1, wherein the water-soluble resin has a weight average molecular weight of 5,000 to 5,000,000.

5. The hair cosmetic material of claim 1, wherein the water soluble-resin is capable of forming an aqueous solution having a concentration of at least 5% by weight.

6. The hair cosmetic material of claim 1, wherein the vinylic monomer (A) is hydroxyethyl acrylamide, and
the vinylic monomer (B) is at least one selected from the group consisting of (meth)acroyloxyethyltrimethylammonium chloride, acroylaminopropyltrimethylammonium chloride, and (meth)acroylaminopropyltrimethylammonium chloride.

7. The hair cosmetic material of claim 1, further comprising an anionic surfactant.

8. The hair cosmetic material of claim 1, wherein the water-soluble resin has a concentration of 0.05 to 5% by weight.

9. The hair cosmetic material of claim 8, further comprising an anionic surfactant at a concentration of 5 to 40% by weight.

10. The hair cosmetic material of claim 1, wherein the copolymer comprises from 20 to 90% by weight of the structural unit corresponding to the vinylic monomer (A).

11. The hair cosmetic material of claim 1, wherein the vinylic monomer (A) is represented by a formula, $CH_2=C(R^1)-CO-NR^2-(CH_2)_2-OH$, where $R^1$ represents a hydrogen atom or a methyl group, and $R^2$ represents a hydrogen atom.

12. The hair cosmetic material of claim 1, wherein $R^4$ and $R^5$ in the formula, $CH_2=C(R^3)-CO(O)_b-(NH)_{1-b}-(CH_2)_c-N^+R^4R^5R^6.X^-$, are each independently a methyl group or an ethyl group, and
$R^6$ in the formula, $CH_2=C(R^3)-CO(O)_b-(NH)_{1-b}-(CH_2)_c-N^+R^4R^5R^6.X^-$, is a methyl group, an ethyl group or a butyl group.

13. The hair cosmetic material of claim 1, further comprising silicone oil.

14. The hair cosmetic material of claim 13, wherein a concentration of the water-soluble resin is controlled to produce a silicone oil adsorption amount on hairs of 70 ppm or more.

15. The hair cosmetic material of claim 13, wherein a concentration of the water-soluble resin is controlled to produce a silicone oil adsorption amount on hairs of 5,000 ppm or less.

16. The hair cosmetic material of claim 1, further comprising a cationic surfactant at a concentration of 0.1 to 3% by weight.

17. The hair cosmetic material of claim 1, further comprising a nonionic surfactant at a concentration of 1 to 10% by weight.

18. The hair cosmetic material of claim 1, further comprising water.

19. The hair cosmetic material of claim 1, wherein the vinylic monomer (A) is represented by a formula, $CH_2=C(R^1)-CO-NR^2-(CH_2)_a-OH$, where $R^1$ represents a hydrogen atom or a methyl group, $R^2$ represents a hydrogen atom, or an alkyl group or a hydroxyalkyl group having 1 to 4 carbon atoms, and a represents an integer from 1 to 4.

20. The hair cosmetic material of claim 19, wherein a in the formula is 2.

21. The hair cosmetic material of claim 1, wherein the monomer mixture comprising the vinylic monomer (A) and the vinylic monomer (B) comprises 20 to 90% by weight of the vinylic monomer (A) and 10 to 80% by weight of the vinylic monomer (B).

* * * * *